(12) United States Patent
Prasser et al.

(10) Patent No.: US 10,086,130 B2
(45) Date of Patent: Oct. 2, 2018

(54) BLOOD OXYGENATOR DEVICE

(71) Applicant: Christopher Prasser, Regensburg (DE)

(72) Inventors: Christopher Prasser, Regensburg (DE); Andreas Redel, Regensburg (DE)

(73) Assignee: Christopher Prasser, Regensburg (DE)

( * ) Notice: Subject to any disclaimer, the term of this patent is extended or adjusted under 35 U.S.C. 154(b) by 7 days.

(21) Appl. No.: 15/323,398

(22) PCT Filed: Jul. 7, 2015

(86) PCT No.: PCT/EP2015/065487
§ 371 (c)(1),
(2) Date: Dec. 30, 2016

(87) PCT Pub. No.: WO2016/005393
PCT Pub. Date: Jan. 14, 2016

(65) Prior Publication Data
US 2017/0136172 A1 May 18, 2017

(30) Foreign Application Priority Data
Jul. 9, 2014 (EP) ..................................... 14176358

(51) Int. Cl.
*G01N 33/48* (2006.01)
*A61M 1/36* (2006.01)
(Continued)

(52) U.S. Cl.
CPC ......... *A61M 1/3666* (2013.01); *A61B 5/0075* (2013.01); *A61B 5/4821* (2013.01);
(Continued)

(58) Field of Classification Search
CPC ...... G01N 21/53; G01N 21/51; G01N 21/532; G01N 15/1434; G01N 15/0205
(Continued)

(56) References Cited

U.S. PATENT DOCUMENTS 3,927,981 A * 12/1975 Viannay .............. A61M 1/1698
128/DIG. 3
5,591,399 A 1/1997 Goldman et al.
(Continued)

FOREIGN PATENT DOCUMENTS

EP 1402909 6/2006
GB 2470757 12/2010
(Continued)

OTHER PUBLICATIONS

European Search Report and Opinion dated Jan. 6, 2015, in European Patent Application No. 14176358.1, 7 pages.
(Continued)

*Primary Examiner* — Md M Rahman
(74) *Attorney, Agent, or Firm* — Lowe Graham Jones PLLC

(57) ABSTRACT

The present invention relates to a blood oxygenator device comprising an equilibration-measurement unit for determining the concentration of an inhalational anesthetic in the blood of a patient, a method of manufacturing such a blood oxygenator device and methods of using such a blood oxygenator device.

20 Claims, 6 Drawing Sheets

(51) Int. Cl.
  *A61B 5/00*       (2006.01)
  *A61M 1/16*       (2006.01)
  *G01N 33/49*      (2006.01)
  *G01N 21/3577*    (2014.01)
  *G01N 21/65*      (2006.01)
  *G01N 29/24*      (2006.01)

(52) U.S. Cl.
  CPC ....... *A61M 1/1698* (2013.01); *G01N 21/3577* (2013.01); *G01N 21/65* (2013.01); *G01N 29/2418* (2013.01); *G01N 33/4925* (2013.01); *A61M 2202/0241* (2013.01); *A61M 2205/3306* (2013.01)

(58) Field of Classification Search
  USPC .......................................... 356/339
  See application file for complete search history.

(56) References Cited

U.S. PATENT DOCUMENTS

| | | | |
|---|---|---|---|
| 2006/0052715 A1* | 3/2006 | Krivitski | A61B 5/0275 600/508 |
| 2008/0041381 A1* | 2/2008 | Tham | A61M 16/0051 128/204.23 |
| 2011/0168177 A1* | 7/2011 | Connor | A61M 16/01 128/203.14 |
| 2011/0213264 A1* | 9/2011 | Finneran | A61M 16/04 600/532 |
| 2012/0029409 A1* | 2/2012 | Rada | A61M 1/30 604/6.09 |
| 2012/0318263 A1* | 12/2012 | Jones | A61M 16/01 128/203.12 |
| 2015/0335807 A1* | 11/2015 | Kellum, Jr. | A61M 1/1654 210/632 |

FOREIGN PATENT DOCUMENTS

| | | |
|---|---|---|
| WO | 02/43792 | 6/2002 |
| WO | 03/092776 | 11/2003 |

OTHER PUBLICATIONS

International Search Report and Written Opinion of the International Searching Authority dated Oct. 8, 2015, in International Patent Application No. PCT/EP2015/065487, 13 pages.

* cited by examiner

BLOOD OXYGENATOR DEVICE

CROSS-REFERENCE TO RELATED APPLICATIONS

This application is a U.S. national phase of International Patent Application No. PCT/EP2015/065487, filed Jul. 7, 2015, entitled "BLOOD OXYGENATOR DEVICE;" which claims the benefit of priority from European Patent Application No. 14176358.1, filed Jul. 9, 2014, entitled "BLOOD OXYGENATOR DEVICE," the contents of which applications are hereby incorporated by reference in their entireties.

FIELD OF THE INVENTION

The present invention relates to the field of extracorporeal blood circuit devices. In particular, the present invention relates to a blood oxygenator device comprising an equilibration-measurement unit for determining the concentration of an inhalational anesthetic in the blood of a patient, a method of manufacturing such a blood oxygenator device and methods of using such a blood oxygenator device.

BACKGROUND OF THE INVENTION

General anesthesia is a medically induced coma and loss of protective reflexes resulting from the administration of one or more anesthetic agents. General anesthesia enables a patient to tolerate surgical procedures that would otherwise inflict unbearable pain or enables surgeons to perform complex procedures by ensuring that the patient does not move during surgery.

Adequate dosage of anesthetic agents during general anesthesia is essential. Underdosage of anesthetics may lead to an insufficient depth of anesthesia and thereby increases the risk of intraoperative awareness. Overdosage, on the other hand, may result in overly deep anesthesia and can even have toxic effects on the patient. Thus, precise monitoring of the blood level of anesthetics is indispensable.

Anesthetic agents may be administered by various routes, e.g. by injection, inhalation, oral administration or rectal administration.

Anesthetics applied by inhalation (inhalational anesthetics) typically show very steep dose-response curves and have the advantage that the depth of anesthesia can be rapidly altered by changing the inhaled concentration of the anesthetic. This means, however, that tight monitoring of the blood level of such inhalational anesthetics is of particular importance.

In inhalation anesthesia during surgical procedures carried out in the absence of a heart-lung machine (cardiopulmonary bypass machine), the blood level of inhalational anesthetics can be monitored by analysis of inspiratory and end-expiratory respiratory gases. The end-expiratory concentration of an inhalational anesthetic agent equals the alveolar concentration which, provided unrestricted pulmonary perfusion, correlates with the blood concentration of the inhalational anesthetic. In clinical practice, the end-expiratory concentration of inhalational anesthetics is therefore often used as surrogate parameter for the blood concentration of the inhalational anesthetic. A prerequisite for successful implementation of this approach is, however, unrestricted blood flow through the lungs of the patient.

Due to, amongst other reasons, the cardioprotective properties of certain inhalational anesthetics, anesthesia with inhalational anesthetic agents has also become a valued option for surgical interventions carried out in the presence of a heart-lung machine. A heart-lung machine is used to establish an extracorporeal circulation (ECC) system in surgical procedures that may necessitate the interruption or cessation of blood flow in the body, a critical organ (such as the heart, lungs or liver) or great blood vessel (such as the aorta, pulmonary artery, pulmonary veins or vena cava), e.g. in coronary artery bypass grafting (CABG) surgery, in particular in cardiac bypass surgery. The heart-lung machine temporarily assumes the functions of the heart and lungs of the patient, wherein the function of the heart, i.e. pumping the blood, is taken over by a mechanical pump, and the function of the lungs, i.e. supplying the blood with oxygen and eliminating accumulating carbon dioxide, is taken over by an oxygenator (N. Kouchoukos et al., Kirklin and Baratt-Boyes: Cardiac Surgery, 4th ed., Saunders (2013); J. Kaplan et al., Kaplan's Cardiac Anesthesia, 6th ed., Saunders (2011)). (Besides surgical interventions in the presence of a heart-lung machine, extracorporeal circulation in the presence of an oxygenator is also used in other medical procedures, for example during extracorporeal membrane oxygenation (ECMO) or pumpless extracorporeal lung assist (PECLA).)

An oxygenator comprises an oxygenating chamber in which gas exchange between a gas flow providing a supply of fresh gas and the blood of a patient takes place. Blood from the body of the patient is pumped to the oxygenator, enters the oxygenating chamber through a blood inlet, passes through the oxygenating chamber, leaves the oxygenating chamber again through a blood outlet and is returned from the oxygenator to the patient. Moreover, a gas flow of fresh gas enters the oxygenating chamber through a gas inlet, is passed through the oxygenating chamber and leaves the oxygenating chamber again through a gas outlet. In the oxygenating chamber, oxygen (and, if present in the gas flow, other gases such as inhalational anesthetics) are transferred from the gas flow into the blood, while other gases, such as carbon dioxide, are transferred from the blood into the gas flow.

There are several types of oxygenators that differ by the way how gas exchange in the oxygenating chamber is accomplished. In bubble oxygenators, gas exchange in the oxygenating chamber is achieved by bubbling the gas of the gas flow through the blood, thus allowing for direct diffusion between the gas bubbles and the blood. Modern-day oxygenators are, however, usually membrane oxygenators in which gas exchange in the oxygenating chamber occurs through a semi-permeable membrane that is permeable to gases like oxygen, carbon dioxide or inhalational anesthetics, but impermeable to blood. Typically, the oxygenating chamber of such a membrane oxygenator comprises a system of hollow fibers formed from the semi-permeable membrane (or, alternatively, membranes formed in other hollow shapes, such as hollow sheets). A gas flow is passed through the inside lumen of the hollow fibers, while blood flows by on the outside of the hollow fibers. Oxygen (and, if present in the gas flow, other gases) diffuse from the gas flowing inside the hollow fibers down their concentration gradient across the membrane wall of the fibers into the blood flowing outside the hollow fibers, while gases that are present in the blood in high concentration, such as carbon dioxide, diffuse down their concentration gradient from the blood into the gas flowing inside the fibers and are removed when the gas flow leaves the oxygenation chamber.

In order to administer an inhalational anesthetic agent to a patient undergoing extracorporeal circulation involving an oxygenator, the inhalational anesthetic can be admixed to the gas flow before leading it through the oxygenating chamber, thus resulting in transfer of the inhalational anesthetic from the gas flow into the blood of the patient. If the inhalational anesthetic agent is a volatile anesthetic, the volatile anesthetic may be vaporized with a vaporizer prior to admixing it to the gas flow.

For inhalation anesthesia of a patient under extracorporeal circulation, the inhalational anesthetic is admixed to the flow of fresh gas fed into the oxygenator of the heart-lung machine at a selected concentration (such as 2% by volume of sevoflurane) and enters the blood of the patient through the oxygenator membrane which is permeable to the inhalational anesthetic. Since under extracorporeal circulation the lungs are not or not fully perfused, it is not possible during ECC to monitor the depth of an anesthesia with inhalational anesthetics by analysis of end-expiratory respiratory gases from the lungs. Alternative methods for monitoring the depth of anesthesia, such as repeated measurement of the concentration of inhalational anesthetics in whole blood by gas chromatography, are not practically feasible.

An alternative approach that has been pursued is to measure the concentration of inhalational anesthetics in the exhaust gas flow of the oxygenator. However, this method can at best be used to verify if a setting at the vaporizer used for vaporizing a volatile anesthetic results in approximately the desired concentration of volatile anesthetic in the flow of fresh gas that is used for gas exchange in the oxygenator. It does not allow accurate conclusions about the amount of inhalational anesthetic that is present in the blood of the patient.

SUMMARY OF THE INVENTION

Thus, there is a need in the art for improved ways to protect against underdosage or overdosage of inhalational anesthetics during inhalation anesthesia of a patient who is under extracorporeal circulation. Moreover, there is a need in the art for improved (such as more accurate and/or faster) ways for determining the concentration of an inhalational anesthetic in the blood of a patient undergoing extracorporeal circulation while said patient is anesthesized with an inhalational anesthetic agent. Moreover, there is a need in the art for improved (such as more accurate, faster and/or more continuous) ways for monitoring the depth of anesthesia of a patient undergoing extracorporeal circulation while said patient is anesthesized with an inhalational anesthetic agent. Moreover, there is a need in the art for improved ways of manipulating the concentration of gases dissolved in the blood of a patient and determining the concentration of an inhalational anesthetic in the blood of a patient, in particular of a patient undergoing extracorporeal circulation. Moreover, there is a need in the art for improved ways of anesthesizing a patient by inhalation anesthesia and monitoring the depth of the resulting anesthesia, wherein said patient is a patient undergoing extracorporeal circulation. Such needs exist in particular in the case of patients undergoing extracorporeal circulation involving a cardiopulmonary bypass machine, patients undergoing extracorporeal circulation in conjunction with extracorporeal membrane oxygenation (ECMO) or patients undergoing extracorporeal circulation in conjunction with pumpless extracorporeal lung assist (PECLA).

These objects are solved by the below-described aspects of the present invention, in particular by a blood oxygenator device according to claim 1, a method of manufacturing a blood oxygenator device according to claim 14 and the use of a blood oxygenator device according to claim 15. Preferable embodiments are defined in the dependent claims.

As used herein, the terms "oxygenator" and "blood oxygenator" are used synonymously and refer to the medical blood gas exchange apparatus that is used to manipulate and/or maintain the level of oxygen and other gases, such as inhalational anesthetics, in the blood of a patient during surgery under extracorporeal circulation, for example during coronary artery bypass graft (CABG) surgery (such as cardiac by-pass surgery), valve repair or valve replacement, but also during extracorporeal membrane oxygenation (ECMO) or pumpless extracorporeal lung assist (PECLA). Preferably, the terms refer to a membrane oxygenator as described above. An "oxygenating chamber" is the portion within an oxygenator in which gas exchange (in particular oxygen, carbon dioxide and NOx exchange, but also exchange of inhalational anesthetics) between the blood flow through the oxygenator and the gas flow through the oxygenator takes place.

The term "blood oxygenator device" is used herein to refer to an assembly that comprises component(s) providing the functionality of an oxygenator (i.e. with the capability of manipulating and/or maintaining the level of oxygen and other gases, such as inhalational anesthetics, in the blood of a patient during surgery under extracorporeal circulation, for example during heart by-pass surgery, during extracorporeal membrane oxygenation (ECMO) or during pumpless extracorporeal lung assist (PECLA)), plus optionally other components, such as an equilibration-measurement unit for determining the concentration of an inhalational anesthetic in blood flowing through the blood oxygenator device. Preferably, the component providing the functionality of an oxygenator is an oxygenating chamber. In some embodiments, the different components of the blood oxygenator device are mounted to the same base plate and/or enclosed in the same housing. In other embodiments, the different components of the blood oxygenator device are not mounted to the same base plate and/or not enclosed in the same housing.

The terms "inhalational anesthetic" and "inhalational anesthetic agent" are used interchangeably and refer to an anesthetic agent that is administered to a patient by inhalation. Examples of inhalational anesthetics are anesthetic gases, such as xenon or nitrous oxide (laughing gas), and volatile anesthetic agents, such as sevoflurane, desflurane, isoflurane or enflurane. The terms "volatile anesthetic" and "volatile anesthetic agent" are used interchangeably and refer to an inhalational anesthetic agent that is liquid at room temperature, but evaporates easily for administration by inhalation. Examples of volatile anesthetics include sevoflurane, desflurane, isoflurane or enflurane.

At several instances, the present invention refers to a situation where a "gas phase does not undergo gas exchange with the environment" except for gas exchange with the blood flowing through the equilibration-measurement unit. This is meant to refer to a situation where (substantially) no gas from said gas phase leaves the gas phase except for gas that passes from the gas phase to the blood flowing through the equilibration-measurement unit and (substantially) no gas from outside of said gas phase is added to said gas phase except for gas that passes from the blood flowing through the equilibration-measurement unit to the gas phase. The skilled person will appreciate that the blood oxygenator device will have to be constructed such that there will nevertheless be provided for (deliberate) gas exchange to an aspirator, if present, (deliberate) gas exchange to deliver gas from the gas phase to an apparatus for determining the concentration of an inhalational anesthetic in the gas phase, if required due to the arrangement of the components of the equilibration-measurement unit, and/or (deliberate) gas exchange through an apparatus for pressure compensation, if present.

Similarly, if the present application states that the "second compartment is configured such that no gas exchange of the gas phase with the environment occurs except for gas exchange through the membrane with blood passing through the first compartment", this is meant to refer to a situation where the second compartment is configured such that (substantially) no gas from said gas phase leaves the gas phase except for gas that passes from the gas phase through the membrane to the blood passing through the first compartment and (substantially) no gas from outside of said gas phase is added to said gas phase except for gas that passes from the blood flowing through the first compartment to the gas phase. The skilled person will appreciate that the second compartment will have to be constructed such that there will nevertheless be provided for (deliberate) gas exchange to an aspirator, if present, (deliberate) gas exchange to deliver gas from the gas phase to an apparatus for determining the concentration of an inhalational anesthetic in the gas phase, if required due to the arrangement of the components of the equilibration-measurement unit, and/or (deliberate) gas exchange through an apparatus for pressure compensation, if present.

When the present invention refers to a blood flow being "split up into two parts", this relates to a situation where the blood flow is divided up into two individual blood flows. When the present invention refers to the two parts of a split-up blood flow being "merged again", this relates to a situation where the two individual blood flows resulting from splitting up the blood flow into two parts are reunited again into a single blood flow. When the present invention refers to "the ratio of the volume of blood passing through the gas exchange chamber to the volume of blood passing through the equilibration-measurement unit" this refers to the number obtained when the volume of blood flowing through the gas exchange chamber during a certain time period is divided by the volume of blood flowing through the equilibration-measurement unit during the same time period. Similarly, when the present invention refers to "ratio of the volume of blood that passes through the equilibration-measurement unit to the volume of blood that bypasses the equilibration-measurement unit" this refers to the number obtained when the volume of blood flowing through the equilibration-measurement unit during a certain time period is divided by the volume of blood bypassing the equilibration-measurement unit during the same time period.

At several instances, the present invention refers to a "patient undergoing extracorporeal circulation". This refers to a situation where part of the circulation of the blood of said patient takes place outside the body of said patient, for example if blood of the patient is passed through a cardiopulmonary bypass machine or during extracorporeal membrane oxygenation (ECMO) or during pumpless extracorporeal lung assist (PECLA).

The term "cardiopulmonary bypass machine", as used herein, refers to a medical device that temporarily takes over the function of the heart and lungs during surgery, maintaining the circulation of blood and the oxygen content of the body (and, possibly, manipulating the content of other gases in the body, such as the content of an inhalational anesthetic agent).

The term "fluid line", as used herein, is meant to designate a conduit or hose for transporting a flow of a liquid, in particular a blood flow. A fluid line for transporting a blood flow can, for example, be a polyvinyl chloride tubing.

The term "surrogate parameter", as used herein, refers to a parameter that correlates with a parameter of interest and that can be measured more easily or more quickly than the parameter of interest. In clinical practice, the surrogate parameter is measured and used as a qualitative or quantitative estimate for the parameter of interest or to monitor changes in the parameter of interest. For example, the end-expiratory concentration of an inhalational anesthetic agent equals the alveolar concentration which, provided unrestricted pulmonary perfusion, correlates with the blood concentration of the inhalational anesthetic. Thus, in clinical practice the end-expiratory concentration of inhalational anesthetics is often used as surrogate parameter for the blood concentration of the inhalational anesthetic, for monitoring changes in the blood concentration of the inhalational anesthetic or to monitor the depth of anesthesia.

In a first aspect, the present invention relates to a blood oxygenator device comprising
  a gas exchange chamber in which gas exchange between a gas flow through said gas exchange chamber and blood of a patient passing through said gas exchange chamber takes place; and
  an equilibration-measurement unit, wherein blood of the patient flows through the equilibration-measurement unit, wherein the equilibration-measurement unit comprises a gas phase which is in contact with the blood flowing through the equilibration-measurement unit such that equilibration with respect to an inhalational anesthetic present in the blood occurs between the blood flowing through the equilibration-measurement unit and the gas phase, and wherein said equilibration-measurement unit comprises an apparatus for determining the concentration of said inhalational anesthetic in the gas phase.

The gas exchange chamber is configured such that a gas flow and blood of a patient can be passed through it and that, when a gas flow and blood of a patient are passed through the gas exchange chamber, gas exchange between the gas flow and the blood of the patient occurs. This can be achieved by constructing the gas exchange chamber like the oxygenating chamber of a conventional blood oxygenator as known in the prior art and/or as described above. For example, the gas exchange chamber can be configured like the oxygenating chamber of a bubble oxygenator or a membrane oxygenator. Preferably, the gas exchange chamber is configured like the oxygenating chamber of a membrane oxygenator.

Blood flow to and from the blood oxygenator device, to and from the gas exchange chamber and to and from the equilibration-measurement unit can be achieved by feeding the blood through fluid lines made from a material that is inert with respect to blood, impermeable to blood and (substantially) impermeable to gases dissolved in blood, such as tubing made from a suitable polymeric material, e.g. polyvinyl chloride tubing. In a sequential arrangement of the equilibration-measurement unit and the gas exchange chamber (as shown for example in FIG. 3 or 4 below), the equilibration-measurement unit and the gas exchange chamber may alternatively be directly attached to each other without any connecting fluid line or tubing in between.

Typically, the gas phase will be contained within an equilibration chamber in the equilibration-measurement unit. The walls of the equilibration chamber separate the gas phase from the environment, from other parts of the equilibration-measurement unit and from the blood flowing through the equilibration-measurement unit.

The skilled person will appreciate that, to allow for equilibration of an inhalational anesthetic to occur between the blood flowing through the equilibration-measurement unit and the gas phase contained in the equilibration-measurement unit, free exchange of the gas phase with gas in the environment of the equilibration-measurement unit has to be minimized, preferably excluded, except for gas exchange through the blood flowing through the equilibration-measurement unit (and controlled gas exchange to an aspirator, if present, gas exchange to deliver gas from the gas phase to the apparatus for determining the concentration of an inhalational anesthetic in the gas phase, if required, and/or gas exchange through an apparatus for pressure compensation, if present), because otherwise no equilibrium can be reached (and because otherwise the concentration of gas in the blood might be altered). To this end, the gas phase may be enclosed by walls that reduce, preferably prevent, gas exchange with the environment, except for gas exchange with the blood flowing through the equilibration-measurement unit. Preferably, the gas phase does (substantially) not undergo gas exchange with the environment, except for gas exchange with the blood flowing through the equilibration-measurement unit and, preferably, except for gas exchange to an aspirator, if present, gas exchange to deliver gas from the gas phase to the apparatus for determining the concentration of an inhalational anesthetic in the gas phase, and/or gas exchange through an apparatus for pressure compensation, if present. Preferably, said equilibration-measurement unit is constructed such that no sweep gas flow through said equilibration-measurement unit can occur.

The gas phase of the equilibration-measurement unit should be under about the same pressure as the environmental air. If the pressure in the gas phase is too high, gas bubbles may develop in the blood phase, whereas if the pressure in the gas phase is too low, there is an increased risk that blood/blood plasma may penetrate through the membrane. To avoid undesired buildup of overpressure or underpressure in the gas phase of the equilibration-measurement unit compared to the environment, the equilibration-measurement unit preferably comprises an apparatus for pressure compensation. The apparatus for pressure compensation compensates for/releases overpressure or underpressure that may build up in the gas phase of the equilibration-measurement unit compared to the environment. In some embodiments, said apparatus for pressure compensation may be an opening that connects the gas phase with the environmental air. The skilled person will appreciate that such an opening has to be such that gas exchange between the gas phase and the environmental air is small enough not to significantly alter the concentration of the gas(es) to be measured in the gas phase and thus not to distort the results obtained. Preferably said apparatus for pressure compensation comprises or consists of a valve, preferably a pressure release valve (i.e. a valve that allows to release overpressure or underpressure in the gas phase of the equilibration-measurement unit compared to the environment). Preferably, said valve is designed such that gas exchange between the gas phase and the environmental air is kept as low as possible while still making sure that buildup of overpressure or underpressure in the gas phase/equilibration chamber of the equilibration-measurement unit compared to the environment is prevented.

As the skilled person will appreciate from the above, said gas exchange chamber and said equilibration-measurement unit are two different parts of said oxygenator device (i.e. said gas exchange chamber and said equilibration-measurement unit are two distinct entities, said gas exchange chamber is not part of said equilibration-measurement unit and said equilibration-measurement unit is not part of said gas exchange chamber).

Preferably, said gas of said gas phase is not absorbed to another material. Preferably, said gas of said gas phase is not present within a matrix.

In one embodiment, said equilibration-measurement unit does not comprise and is not connected to any gas inlets for changing the gas composition of the gas phase contained in said equilibration-measurement unit. In one embodiment, said equilibration-measurement unit does not comprise and is not connected to any feed gas inlet. In one embodiment, said equilibration-measurement unit does not comprise and is not connected to any gas inlet for adding gas of a composition that is different than the composition of the gas phase contained in said equilibration-measurement unit (except for (deliberate) gas exchange through an apparatus for pressure compensation, if present).

In one embodiment, said equilibration-measurement unit does not comprise and/or is not connected to any gas inlets or outlets that allow to add or remove gas from the gas phase of said equilibration-measurement unit (except for gas exchange with the blood flowing through the equilibration-measurement unit).

In one embodiment, said equilibration-measurement unit does not comprise a gas inlet and, preferably, does not comprise a gas outlet. Thus, the gas phase contained in the equilibration-measurement unit does not undergo any gas exchange except for the gas exchange with the blood flowing through the equilibration-measurement unit. This has the effect that the composition of the gas phase contained in the equilibration-measurement is only influenced by the concentration of gases in the blood flowing through the equilibration-measurement unit.

The apparatus for determining the concentration of said inhalational anesthetic in the gas phase may be a sensor that can determine the concentration of the inhalational anesthetic in the gas phase by optical methods (e.g. IR-spectroscopy, Raman spectroscopy or combinations thereof), by acoustic measurements (e.g. photoacoustic infrared spectroscopy), by mass spectrometry (e.g. by multicomponent analysis with an AirSense® ion-molecule reaction mass spectrometer (V&F Analyse and Messtechnik GmbH of Absam, Austria)) or by measurements with a semiconductor gas sensor.

According to the prior art, changes in the concentration of an inhalational anesthetic in the blood of a patient are monitored by measuring the concentration of inhalational anesthetics in the end-expiratory respiratory gases. The concentration of inhalational anesthetics in the end-expiratory respiratory gases corresponds to the alveolar concentration of the inhalational anesthetic, and since the changes of the alveolar concentration directly mirror changes in the blood concentration of the inhalational anesthetic, the alveolar concentration of the inhalational anesthetic is used in clinical practice as surrogate parameter for the blood concentration of the inhalational anesthetic. Thus, while the manipulations by the anesthesist are directed at the concentration of the inhalational anesthetic in the blood and brain of the patient, the parameter monitored is the surrogate parameter, i.e. the alveolar concentration of the inhalational anesthetic (in volume percent). The concentration of inhalational anesthetic as determined from the gas phase of the equilibration-measurement unit of the present invention equals the alveolar concentration of the inhalational anesthetic under full perfusion of the lungs and accordingly provides the same surrogate parameter information as the alveolar concentration, thus allowing to monitor changes in the blood concentration of the inhalational anesthetic. Alternatively, the concentration of the inhalational anesthetic in the blood of the patient flowing through the equilibration-measurement unit can be calculated from the concentration of the inhalational anesthetic in the gas phase of the equilibration-measurement unit by standard methods through the blood-gas partition coefficient of the inhalational anesthetic at the particular conditions (Millers Anesthesia, Ronald D. Miller, 7th ed. 2010, page 540). Alternatively, the concentration of the inhalational anesthetic in the blood of the patient flowing through the equilibration-measurement unit can be obtained through a standard curve according to common techniques known to the person of skill in the art. For example, the concentration of the inhalational anesthetic in the gas phase of the equilibration-measurement unit can be measured at different blood concentrations of the inhalational anesthetic in a patient, while at the same time samples of the blood flowing through the equilibration-measurement unit are taken. The concentration of the inhalational anesthetic in the blood samples can be determined by gas chromatography. By plotting the values obtained for the concentration of the inhalational anesthetic in the blood samples over the values obtained for the concentration of the inhalational anesthetic in the gas phase of the equilibration-measurement unit in a graph, a standard curve is obtained. This standard curve allows to determine the blood concentration of the inhalational anesthetic from the concentration of the inhalational anesthetic in the gas phase of the equilibration-measurement unit.

Preferably, said patient is a patient under anesthesia, preferably under anesthesia through exposure to an inhalational anesthetic.

In one embodiment, said equilibration-measurement unit comprises a membrane which is impermeable to blood, but permeable to gas. In one embodiment, said equilibration-measurement unit comprises a membrane which is impermeable to blood, but permeable to the inhalational anesthetic.

In some embodiments, said equilibration-measurement unit comprises a first compartment through which the blood flowing through the equilibration-measurement unit passes and a second compartment in which the gas phase is contained, wherein contact between the first compartment and the second compartment is provided by a membrane which is impermeable to blood, but permeable to the inhalational anesthetic. Thus, the walls defining the borders of the second compartment form an equilibration chamber.

Preferably, said membrane is formed from a single material and, preferably, no layer formed from another material is located on said membrane formed from said single material. Preferably, no layer formed from a gas impermeable material is located on said membrane.

This configuration has the advantage that reliable equilibration of gases between the blood flowing through the equilibration-measurement unit and the gas phase contained in the equilibration-measurement unit can be accomplished, while at the same time no liquid from the blood can contaminate the gas phase and/or negatively affect the measurement.

As the skilled person will appreciate, the walls of the first compartment should (except for the part formed by the membrane) be made of a material that is inert and impermeable to both gas (in particular to oxygen, carbon dioxide and inhalational anesthetics) and blood, and may for example be made of glass, steel, polycarbonate, polyurethane, polytetrafluoroethylene, polyethylenenaphthalate (PEN, Teonex®) or a copolymer of PEN and polyethyleneterephthalate (PET). Optionally, MXD6-Nylon or a copolymer of ethylene and vinylalcohol (EVOH) may be admixed, or a coating of MXD6-Nylon or a copolymer of ethylene and vinylalcohol (EVOH) may be added.

The walls of the second compartment should (except for the part formed by the membrane) be made of a material that is inert and impermeable to gas (in particular to oxygen, carbon dioxide and inhalational anesthetics), and may for example be made of glass, steel, polycarbonate, polyurethane, polytetrafluoroethylene, polyethylenenaphthalate (PEN, Teonex®) or a copolymer of PEN and polyethyleneterephthalate (PET). Optionally, MXD6-Nylon or a copolymer of ethylene and vinylalcohol (EVOH) may be admixed, or a coating of MXD6-Nylon or a copolymer of ethylene and vinylalcohol (EVOH) may be added. Preferably, the second compartment of the equilibration-measurement unit is hermetically sealed, with the exception of the region where the second compartment contacts the first compartment through membrane (and, as the skilled person will appreciate, with the exception of the areas where connecting lines to deliver gas from the gas phase to the apparatus for determining the concentration of said inhalational anesthetic in the gas phase, an apparatus for pressure compensation or an aspirator are connected to the second compartment, if present, are connected to the second compartment). In some preferred embodiments, the walls of the second compartment consist almost entirely or entirely of membrane. This may for example be achieved by using a hollow fiber arrangement of the membrane as in membrane oxygenators known in the prior art, wherein the lumen of the hollow fibers serves as second compartment.

As membrane material, materials typically used for membranes in the oxygenating chamber of membrane oxygenators can be used, such as conventional polypropylene membrane (PPL).

As is clear to a person of skill in the art, the membrane does not form any other parts of the walls of the first compartment and of the second compartment than the region of contact between the first compartment and the second compartment.

In some embodiments, the blood oxygenator device is configured such that the blood flow through the blood oxygenator device is split up into two parts, wherein the first part of the blood flow passes through the gas exchange chamber and the second part of the blood flow passes through the equilibration-measurement unit, and wherein, after the first part of the blood flow has passed through the gas exchange chamber and the second part of the blood has passed through the equilibration-measurement unit, the first and the second part of the blood flow are merged again.

The configuration has the advantage that the volume of blood flowing through the gas exchange chamber and the equilibration-measurement unit can be different (which can be achieved, for example, if tubing of different diameter is used for the two branches of the blood flow or if an appliance for controlling the volume of the blood flow is integrated into one or both of the branches of the blood flow), and thus the blood flow can be adjusted appropriately if the gas exchange chamber and the equilibration-measurement unit are designed for different blood volumes. Moreover, this configuration allows to make sure that the use of an equilibration-measurement unit designed for small blood volumes does not have an impact on the blood volume passing through the gas exchange chamber and thus the time for manipulating the gas level of the blood of the patient is not affected.

Preferably, the blood oxygenator device is configured such that the ratio of the volume of blood that passes through the gas exchange chamber to the volume of blood that passes through the equilibration-measurement unit is at least 2, more preferably at least 5, more preferably at least 10, more preferably at least 20, more preferably at least 100. A configuration of the blood oxygenator device resulting in such a ratio of the blood volumes can for example be achieved by using for the fluid lines of the branch passing through the gas exchange chamber a tubing with an appropriately larger diameter than for the fluid lines of the branch passing through the equilibration-measurement unit. By adjusting the ratio of the blood volumes appropriately, it can be ensured that a sufficient fraction of the blood volume flowing through the blood oxygenator device passes through the branch leading through the gas exchange chamber, and thus a high rate of gas exchange with respect to the total volume of blood in the extracorporeal circulation system is achieved.

In some embodiments, the blood oxygenator device is configured such that the blood flow through the blood oxygenator device first passes through the equilibration-measurement unit and subsequently passes through the gas exchange chamber. Compared to a blood flow that first passes through the gas exchange chamber and subsequently passes through the equilibration-measurement unit, this has the advantage that a more accurate measurement of the gas concentrations in the venous blood from the patient's body is obtained.

In some embodiments, the blood oxygenator device is configured such that the blood flow through the blood oxygenator device first passes through the gas exchange chamber and subsequently passes through the equilibration-measurement unit. Compared to a blood flow that first passes through the equilibration-measurement unit and subsequently passes through the gas exchange chamber, this has the advantage that it is possible to find out how efficiently the gas chamber can alter the concentration of an inhalational anesthetic in the blood passing through the blood oxygenator device and is well suited for determining the concentration of the inhalational anesthetic in the arterial blood of the patient and monitoring the depth of narcosis.

In some embodiments, the blood oxygenator device is configured such that the blood flow through the blood oxygenator device is split up into two parts, wherein the first part of the blood flow passes through the equilibration-measurement unit and the second part of the blood flow bypasses the equilibration-measurement unit, and wherein, after the first part of the blood flow has passed through the equilibration-measurement unit and the second part of the blood has bypassed the equilibration-measurement unit, the first and the second part of the blood flow are merged again, wherein, preferably, the blood oxygenator device is configured such that the blood flow through the blood oxygenator device first passes through/bypasses the equilibration-measurement unit and subsequently passes through the gas exchange chamber or such that the blood flow through the blood oxygenator device first passes through the gas exchange chamber and subsequently passes through/bypasses the equilibration-measurement unit.

Preferably, the ratio of the volume of blood that passes through the equilibration-measurement unit to the volume of blood that bypasses the equilibration-measurement unit is no more than 0.5, more preferably no more than 0.2, more preferably no more than 0.1, more preferably no more than 0.05, more preferably no more than 0.01. A configuration of the blood oxygenator device resulting in such a ratio of the blood volumes can for example be achieved by using for the fluid line bypassing the equilibration-measurement unit a tubing with an appropriately larger diameter than for the fluid lines of the branch passing through the equilibration-measurement unit. By adjusting this ratio of the blood volumes appropriately, uninhibited blood flow through the oxygenator device can be achieved while still ensuring sufficient blood flow through the equilibration-measurement unit for accurate measurements.

In some embodiments, said apparatus for determining the concentration of the inhalational anesthetic in the gas phase comprises or consists of a sensor, preferably a sensor for determining the concentration of the inhalational anesthetic in the gas phase by optical measurements, more preferably by IR-spectroscopy or Raman spectroscopy, or by acoustic measurements, more preferably by photoacoustic infrared spectroscopy, or by mass spectrometry or by measurements with a semiconductor gas sensor. The use of such sensors has the advantage that the requirements for aspiration or shunt flow of gas to be analyzed can be obviated and that a compact build can be achieved.

In some embodiments, said equilibration-measurement unit comprises an aspirator that delivers the gas phase or a part of the gas phase to the apparatus for determining the concentration of the inhalational anesthetic in the gas phase. In some embodiments, said gas-phase containing compartment is connected to an aspirator that delivers the gas phase or a part of the gas phase to the apparatus for determining the concentration of the inhalational anesthetic in the gas phase. Preferably, said aspirator is a suction device that delivers a sample of gas from the gas phase to the apparatus for determining the concentration of the inhalational anesthetic in the gas phase. The skilled person will appreciate that, to avoid undesired pressure buildup, an equilibration-measurement unit comprising an aspirator may include an apparatus for pressure compensation, as described above. The use of an aspirator allows to ensure optimal delivery of gas for analysis to the apparatus for determining the concentration of the inhalational anesthetic in the gas phase. Moreover, it allows to use a conventional anesthesia device for determination of the concentration of the inhalational anesthetic in the gas phase, because it allows to deliver gas for analysis to the module for side stream analysis of the conventional anesthesia device (in this case, the module for side stream analysis of the conventional anesthesia device functions as apparatus for determining the concentration of the inhalational anesthetic in the gas phase).

In some embodiments, said aspirator continuously delivers gas of the gas phase to the apparatus for determining the concentration of the inhalational anesthetic in the gas phase. In some embodiments, said aspirator does not continuously deliver gas of the gas phase to the apparatus for determining the concentration of the inhalational anesthetic in the gas phase. In some embodiments, said aspirator delivers gas of the gas phase at certain, preferably regular, time intervals to the apparatus for determining the concentration of the inhalational anesthetic in the gas phase.

Preferably, the volume of gas that is removed from the gas phase by the aspirator and/or used for determining the concentration of the inhalational anesthetic in the gas phase is not more than $1/10$, preferably not more than $1/20$, more preferably, not more than $1/50$, more preferably not more than $1/100$ of the total volume of gas in the gas phase.

In some embodiments, the blood oxygenator device is constructed such that the gas that is removed from the gas phase by the aspirator and/or used for determining the concentration of the inhalational anesthetic in the gas phase is returned to the gas phase/the second compartment/the equilibration chamber after the measurement or after passing through the apparatus for determining the concentration of the inhalational anesthetic in the gas phase or, if an aspirator is present, through the aspirator and the apparatus for determining the concentration of the inhalational anesthetic in the gas phase.

In some embodiments, said aspirator and/or said apparatus for determining the concentration of the inhalational anesthetic in the gas phase and/or said apparatus for pressure compensation are fully integrated into (i.e. located within) said second compartment/said equilibration chamber. In some embodiments, said aspirator and/or said apparatus for determining the concentration of the inhalational anesthetic in the gas phase and/or said apparatus for pressure compensation are located outside of said second compartment/said equilibration chamber.

In some embodiments, the gas phase is enclosed within an equilibration chamber having walls that are permeable to light or having walls that have sections which are permeable to light, such that the concentration of the inhalational anesthetic in the gas phase can be determined spectroscopically through said walls that are permeable to light or through said sections which are permeable to light. This may for example be achieved by light-permeable windows in the walls of the equilibration chamber. Such light-permeable windows may allow to direct light emitted by a light source outside of the equilibration chamber through the gas phase in the equilibration chamber and determine the concentration of the inhalational anesthetic in the gas phase by IR-spectroscopy or spectroscopic measurements based on Raman light scattering with a suitable detector (i.e. an apparatus for determining the concentration of the inhalational anesthetic in the gas phase) located outside of the equilibration chamber once the light has left the equilibration chamber.

In some embodiments, the blood oxygenator device comprises a first oxygenator, wherein said first oxygenator comprises an oxygenating chamber through which a gas flow passes, the oxygenating chamber of said first oxygenator serving as gas exchange chamber of the blood oxygenator device.

In some embodiments, the blood oxygenator device comprises a second oxygenator, wherein said second oxygenator comprises an oxygenating chamber through which no gas flow passes, the oxygenating chamber of said second oxygenator serving as equilibration-measurement unit of the blood oxygenator device.

In some embodiments, the blood oxygenator device comprises a first and a second oxygenator, wherein said first oxygenator comprises an oxygenating chamber through which a gas flow passes, the oxygenating chamber of said first oxygenator serving as gas exchange chamber of the blood oxygenator device, while said second oxygenator comprises an oxygenating chamber through which no gas flow passes, the oxygenating chamber of said second oxygenator serving as equilibration-measurement unit of the blood oxygenator device.

To build a blood oxygenator device according to the latter embodiments, said first oxygenator can be integrated into the blood oxygenator device in a way that allows it to function essentially in the same fashion as a stand-alone oxygenator, thus allowing the oxygenating chamber of said first oxygenator to assume the function of the gas exchange chamber of the blood oxygenator device. In the second oxygenator, the gas inlet of the oxygenating chamber of the second oxygenator can be hermetically closed while the gas outlet of the oxygenating chamber is connected to the apparatus for determining the concentration of the inhalational anesthetic in the gas phase, or the gas outlet of the oxygenating chamber of the second oxygenator can be hermetically closed while the gas inlet of the oxygenating chamber is connected to the apparatus for determining the concentration of the inhalational anesthetic in the gas phase.

In a blood oxygenator device according to the latter embodiments, the first oxygenator and the second oxygenator can be conventional (i.e. off the shelf) blood oxygenators. Such conventional blood oxygenators are readily commercially available and, since they are produced in large unit numbers, relatively inexpensive compared to custom-made components.

Since oxygenators are readily commercially available and since building of a blood oxygenator device according to the above-described embodiment can be achieved with only minor modifications to conventional oxygenators, the blood oxygenator device according to these embodiments has the advantage that it can be assembled from readily available parts and is thus available at a moderate cost.

Preferably, said first oxygenator and/or said second oxygenator is a membrane oxygenator.

Preferably, said first oxygenator is an oxygenator designed for use with adult humans and/or said second oxygenator is an oxygenator designed for use with infant humans or rodents. Oxygenators designed for use with infant humans or rodents are designed for smaller volumes of blood passing through them than oxygenators designed for use with adult humans. Thus, in particular if the gas exchange chamber and the equilibration-measurement unit are arranged such that the blood flow passes through them in parallel, the use of an oxygenator designed for use with infant humans or rodents as second oxygenator has the advantage that an equilibration-measurement unit is obtained that requires only a small blood volume passing through. Moreover, since the use of an oxygenator designed for use with infant humans or rodents as second oxygenator results in a blood oxygenator device with a small volume of the gas phase, equilibration of the gas phase is achieved more quickly, such that equilibration-measurement unit is capable of faster detection of changes in the concentration of inhalational anesthetics in the blood. Moreover, if the first oxygenator is an oxygenator designed for use with adult humans and the second oxygenator is an oxygenator designed for use with infant humans or rodents, it can be made sure that the bulk of the blood volume flowing through the blood oxygenator device passes through the gas exchange chamber and thus efficient oxygenation of the total blood volume in the extracorporeal circulation system is achieved.

In some embodiments, the blood oxygenator device comprises a vaporizer for vaporizing a volatile anesthetic.

In some embodiments, the blood oxygenator device comprises an apparatus for admixing the inhalational anesthetic (preferably the vaporized volatile anesthetic) to the gas flow used for gas exchange in the gas exchange chamber.

In some embodiments, the blood oxygenator device comprises a heat exchanger. The heat exchanger allows to manipulate the temperature of the blood flowing through the blood oxygenator device.

In some embodiments, said inhalational anesthetic is an anesthetic gas, preferably xenon or nitrous oxide (laughing gas). In some embodiments, said inhalational anesthetic is a volatile anesthetic, preferably a volatile anesthetic selected from the group consisting of sevoflurane, desflurane, isoflurane, enflurane and halothane.

In some embodiments, the gas exchange chamber and the equilibration-measurement unit are attached to the same base plate and/or enclosed in the same housing. Preferably, also the vaporizer for vaporizing a volatile anesthetic and/or the apparatus for admixing the inhalational anesthetic (preferably the vaporized volatile anesthetic) to the gas flow used for gas exchange in the gas exchange chamber are assembled on the same base plate as the gas exchange chamber and the equilibration-measurement unit and/or enclosed in the same housing as the gas exchange chamber and the equilibration-measurement unit.

In some embodiments, said gas exchange chamber is capable of mediating gas exchange with respect to oxygen, carbon dioxide and/or an inhalational anesthetic/inhalational anesthetics between the gas flow through said gas exchange chamber and blood of a patient passing through said gas exchange chamber.

In some embodiments, said blood oxygenator device is for one or more of the following:
  adjusting the concentration of gases dissolved in the blood of a patient;
  determining a surrogate parameter for the concentration of an inhalational anesthetic in the blood of a patient;
  monitoring changes in the concentration of an inhalational anesthetic in the blood of a patient;
  determining the concentration of an inhalational anesthetic in the blood of a patient;
  monitoring the depth of anesthesia of a patient;
wherein, preferably, said patient is a patient undergoing extracorporeal circulation, more preferably a patient undergoing extracorporeal circulation involving a cardiopulmonary bypass machine, a patient undergoing extracorporeal circulation in conjunction with extracorporeal membrane oxygenation (ECMO) or a patient undergoing extracorporeal circulation in conjunction with pumpless extracorporeal lung assist (PECLA).

In some embodiments, said blood oxygenator device is for carrying out extracorporeal circulation involving a cardiopulmonary bypass machine, preferably for use during heart surgery. In some embodiments, said blood oxygenator device is for carrying out extracorporeal circulation in conjunction with extracorporeal membrane oxygenation (ECMO) or extracorporeal circulation in conjunction with pumpless extracorporeal lung assist (PECLA).

In some embodiments, said blood oxygenator device is for monitoring the depth of anesthesia of a patient, preferably a patient undergoing extracorporeal circulation, more preferably a patient undergoing extracorporeal circulation involving a cardiopulmonary bypass machine, a patient undergoing extracorporeal circulation in conjunction with extracorporeal membrane oxygenation (ECMO) or a patient undergoing extracorporeal circulation in conjunction with pumpless extracorporeal lung assist (PECLA).

As laid out in detail above, the concentration of inhalational anesthetic as determined from the gas phase of the equilibration-measurement unit of the present invention is a surrogate parameter for the concentration of the inhalational anesthetic in the blood of a patient and allows to monitor changes in the blood concentration of the inhalational anesthetic. Moreover, the concentration of the inhalational anesthetic in the blood of a patient flowing through the equilibration-measurement unit can be calculated from the concentration of the inhalational anesthetic in the gas phase of the equilibration-measurement unit of the present invention through the blood-gas partition coefficient of the inhalational anesthetic or obtained through a standard curve, as described above.

In a second aspect, the present invention relates to a method of manufacturing a blood oxygenator device according to the invention comprising the steps of
a) providing a gas exchange chamber configured to allow for gas exchange between a gas flow through said gas exchange chamber and blood of a patient passing through said gas exchange chamber;
b) providing an equilibration-measurement unit comprising
  a first compartment configured to allow for blood passing through it;
  a second compartment in which a gas phase is contained, wherein contact between the first compartment and the second compartment is provided by a membrane which is impermeable to blood, but permeable to an inhalational anesthetic, and wherein, preferably, said second compartment is configured such that (substantially) no gas exchange of the gas phase with the environment occurs except for gas exchange through the membrane with blood passing through the first compartment and, preferably, except for gas exchange to an aspirator, if present, gas exchange to deliver gas from the gas phase to the apparatus for determining the concentration of an inhalational anesthetic in the gas phase, and/or gas exchange through an apparatus for pressure compensation, if present; and
  an apparatus for determining the concentration of an inhalational anesthetic in the gas phase;
c) providing fluid lines for transporting a blood flow;
d) connecting the gas exchange chamber and the equilibration-measurement unit with said fluid lines such that blood can be passed through the gas exchange chamber and the equilibration-measurement unit;
thereby providing a blood oxygenator device.

Preferably, said fluid lines are arranged such that
  the blood flow through the blood oxygenator device is split up into two parts, wherein the first part of the blood flow passes through the gas exchange chamber and the second part of the blood flow passes through the equilibration-measurement unit, and wherein, after the first part of the blood flow has passed through the gas exchange chamber and the second part of the blood has passed through the equilibration-measurement unit, the first and the second part of the blood flow are merged again; or
  the blood flow through the blood oxygenator device first passes through the equilibration-measurement unit and subsequently passes through the gas exchange chamber.
  the blood flow through the blood oxygenator device first passes through the gas exchange chamber and subsequently passes through the equilibration-measurement unit.

In some embodiments, said fluid lines are arranged such that the blood flow through the blood oxygenator device is split up into two parts, wherein the first part of the blood flow passes through the equilibration-measurement unit and the second part of the blood flow bypasses the equilibration-measurement unit, and wherein, after the first part of the blood flow has passed through the equilibration-measurement unit and the second part of the blood has bypassed the equilibration-measurement unit, the first and the second part of the blood flow are merged again, wherein, preferably, the blood oxygenator device is configured such that the blood flow through the blood oxygenator device first passes through/bypasses the equilibration-measurement unit and subsequently passes through the gas exchange chamber, or such that the blood flow through the blood oxygenator device first passes through the gas exchange chamber and subsequently passes through/bypasses the equilibration-measurement unit.

In further embodiments, said gas exchange chamber, said equilibration-measurement unit, said first compartment, said second compartment, said gas phase, said membrane, said inhalational anesthetic and/or said apparatus for determining the concentration of an inhalational anesthetic in the gas phase are as defined in any of the above-described embodiments of the first aspect of the present invention.

Said fluid lines can, for example, be polyvinyl chloride tubing.

In a third aspect, the present invention relates to the use of a blood oxygenator device according to the invention for one or more of the following:
- determining a surrogate parameter for the concentration of an inhalational anesthetic in the blood of a patient;
- monitoring changes in the concentration of an inhalational anesthetic in the blood of a patient;
- determining the concentration of an inhalational anesthetic in the blood of a patient;
- monitoring the depth of anesthesia of a patient;

wherein said use preferably comprises the steps of
a) passing blood of said patient through the equilibration-measurement unit of said blood oxygenator device;
b) determining the concentration of the inhalational anesthetic in the gas phase comprised by said equilibration-measurement unit;
c) based on the concentration of the inhalational anesthetic obtained in step b), determining a surrogate parameter for the concentration of the inhalational anesthetic in the blood of the patient and/or monitoring changes in the concentration of the inhalational anesthetic in the blood of the patient and/or determining the concentration of the inhalational anesthetic in the blood of the patient and/or monitoring the depth of anesthesia of the patient.

In a fourth aspect, the present invention relates to a method of one or more of the following:
- manipulating the concentration of gases dissolved in the blood of a patient;
- determining a surrogate parameter for the concentration of an inhalational anesthetic in the blood of a patient;
- monitoring changes in the concentration of an inhalational anesthetic in the blood of a patient;
- determining the concentration of an inhalational anesthetic in the blood of a patient;
- monitoring the depth of anesthesia of a patient;

wherein, preferably said patient is a patient undergoing extracorporeal circulation, more preferably of a patient undergoing extracorporeal circulation involving a cardiopulmonary bypass machine, a patient undergoing extracorporeal circulation in conjunction with extracorporeal membrane oxygenation (ECMO) or a patient undergoing extracorporeal circulation in conjunction with pumpless extracorporeal lung assist (PECLA), said method comprising:
a) passing blood of said patient and a gas flow through the gas exchange chamber of a blood oxygenator device as defined in any of the embodiments of the present invention, thereby manipulating the concentration of gases dissolved in the blood of said patient;
b) passing blood of said patient through the equilibration-measurement unit of said blood oxygenator device;
c) determining the concentration of the inhalational anesthetic in the gas phase comprised by said equilibration-measurement unit;
d) based on the concentration of the inhalational anesthetic obtained in step c), determining a surrogate parameter for the concentration of the inhalational anesthetic in the blood of the patient and/or monitoring changes in the concentration of the inhalational anesthetic in the blood of the patient and/or determining the concentration of the inhalational anesthetic in the blood of the patient and/or monitoring the depth of anesthesia of the patient.

In a fifth aspect, the present invention relates to a method of anesthesizing a patient and/or monitoring the depth of anesthesia of said patient, wherein said patient is, preferably, a patient undergoing extracorporeal circulation, more preferably a patient undergoing extracorporeal circulation involving a cardiopulmonary bypass machine, a patient undergoing extracorporeal circulation in conjunction with extracorporeal membrane oxygenation (ECMO) or a patient undergoing extracorporeal circulation in conjunction with pumpless extracorporeal lung assist (PECLA), said method comprising:
a) passing blood of said patient and a gas flow containing at least one inhalational anesthetic through the gas exchange chamber of a blood oxygenator device according to the invention, thereby anesthesizing said patient;
b) passing blood of said patient through the equilibration-measurement unit of said blood oxygenator device;
c) determining the concentration of the inhalational anesthetic in the gas phase comprised by said equilibration-measurement unit;
d) optionally, determining, based on the concentration of the inhalational anesthetic obtained in step c), the concentration of the inhalational anesthetic in the blood of the patient;
e) concluding from the concentration of the inhalational anesthetic in the gas phase comprised by said equilibration-measurement unit as obtained in step c) or the concentration of the inhalational anesthetic in the blood of the patient as obtained in step d) on the depth of anesthesia of said patient.

BRIEF DESCRIPTION OF THE FIGURES

The invention is now described with reference to the attached figures, wherein.

DETAILED DESCRIPTION OF PREFERRED EMBODIMENTS

For the purpose of promoting an understanding of the principles of the invention, reference will now be made to the preferred embodiments and specific language will be used to describe the same. It will nevertheless be understood that no limitation of the scope of the invention is intended thereby, such alterations and further modifications in the device and methods and such further applications of the principles of the invention as illustrated therein being contemplated as would normally occur now or in the future to one skilled in the art to which the invention relates.

Moreover, it is to be understood that features and advantages described with regard to one aspect of the invention may also be implied by other aspects of the invention.

Figure 1:
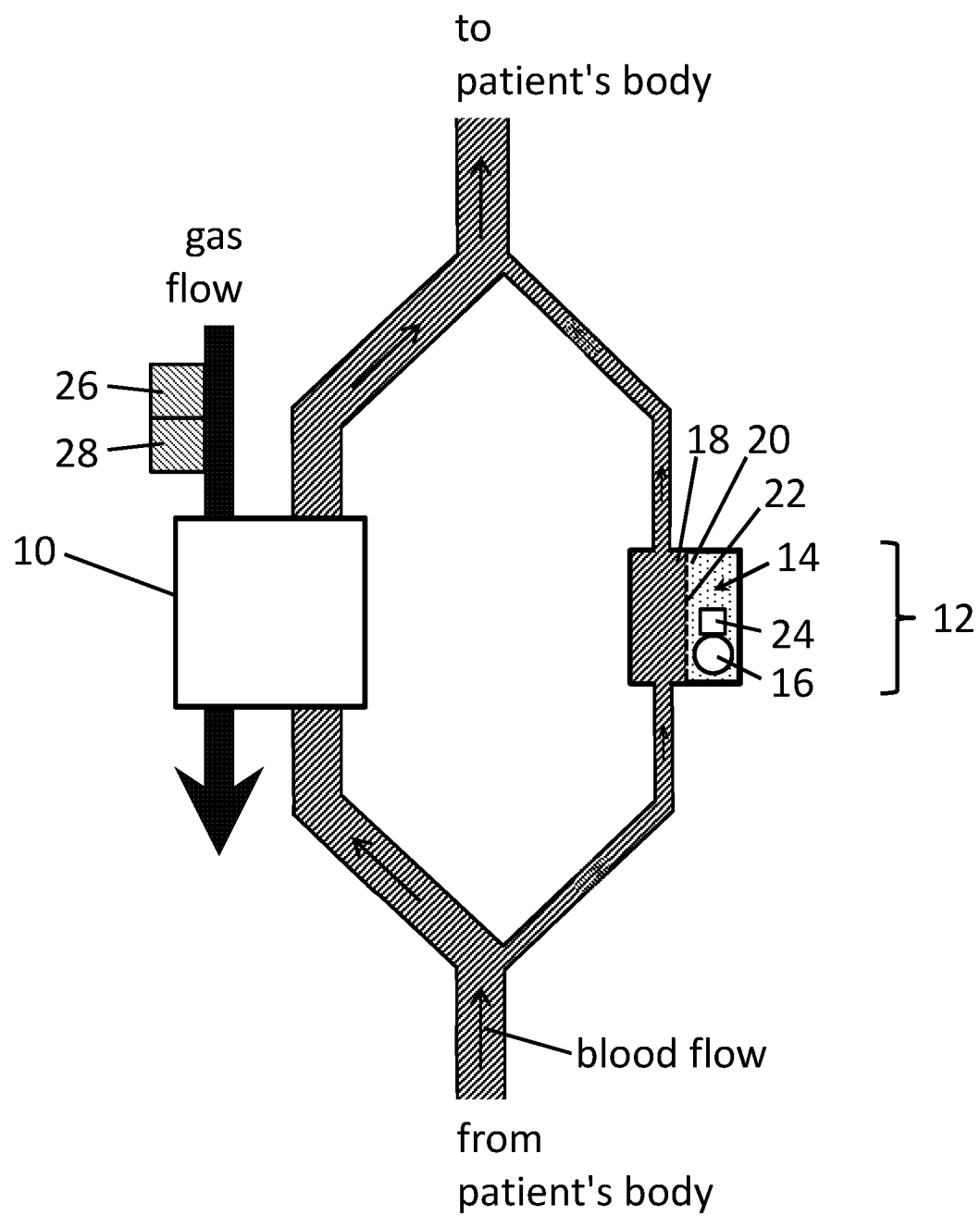
FIG. 1 shows an embodiment of the present invention in which the gas exchange chamber and the equilibration-measurement unit are arranged in parallel.

FIG. 1 shows a blood oxygenator device according to an embodiment of the invention. As seen therein, the blood oxygenator comprises a gas exchange chamber 10 in which gas exchange between a gas flow (shown as a black arrow) through said gas exchange chamber 10 and blood of a patient passing through said gas exchange chamber 10 takes place. By feeding a fresh gas flow of appropriate composition into the gas exchange chamber 10, the concentration of gases in the blood of the patient can be manipulated.

In addition, the blood oxygenator device comprises an equilibration-measurement unit 12 through which blood of the patient flows. The equilibration-measurement unit 12 comprises a gas phase 14 which is in contact with the blood flowing through the equilibration-measurement unit 12 such that equilibration with respect to an inhalational anesthetic present in the blood occurs between the blood flowing through the equilibration-measurement unit 12 and the gas phase 14. Moreover, the equilibration-measurement unit 12 comprises an apparatus 16 for determining the concentration of said inhalational anesthetic in the gas phase 14.

As shown in FIG. 1, the equilibration-measurement unit 12 comprises a first compartment 18 through which the blood flowing through the equilibration-measurement unit 12 passes and a second compartment 20 in which the gas phase 14 is contained. Contact between the first compartment 18 and the second compartment 20 is provided by a membrane 22. This membrane is impermeable to blood, but permeable to the inhalational anesthetic. As a result, equilibration with respect to an inhalational anesthetic present in the blood occurs between the blood flowing through the equilibration-measurement unit 12 and the gas phase 14 can occur.

The second compartment 20 of the equilibration-measurement unit 12 is hermetically sealed, with the exception of the region where the second compartment 20 contacts the first compartment 18 through membrane 22. Moreover, the membrane 22 does not form any other parts of the walls of the first compartment 18 and of the second compartment 20 than the region of contact between the first compartment 18 and the second compartment 20.

The blood oxygenator device is configured such that the blood flow through the blood oxygenator device is split up into two parts. The first part of the blood flow passes through the gas exchange chamber 10 and the second part of the blood flow passes through the equilibration-measurement unit 12. After passing through the gas exchange chamber 10 and the equilibration-measurement unit 12, respectively, the two blood flows are reunited again. As shown in FIG. 1, the diameter of the fluid lines in the branch passing through the gas exchange chamber 10 is larger than that in the branch passing through the equilibration-measurement unit 12, such that the major part of the blood flow through the oxygenator device is led through the gas exchange chamber 10, while only a smaller fraction of the blood flow through the oxygenator passes through the equilibration-measurement unit 12.

According to the embodiment shown in FIG. 1, the apparatus 16 for determining the concentration of the inhalational anesthetic in the gas phase 14 further comprises a sensor and an aspirator 24 that delivers gas from the gas phase 14 to the apparatus 16 for determining the concentration of the inhalational anesthetic in the gas phase 14. In the embodiment depicted in FIG. 1, said aspirator 24 and said apparatus 16 for determining the concentration of the inhalational anesthetic in the gas phase 14 are fully integrated (i.e. located within) the gas-phase containing second compartment 20.

The blood oxygenator device shown in FIG. 1 furthermore comprises a vaporizer 26 for vaporizing a volatile anesthetic that may be used as inhalational anesthetic, and an apparatus 28 for admixing the inhalational anesthetic/vaporized volatile anesthetic to the gas flow used for gas exchange in the gas exchange chamber 10.

Figure 2:
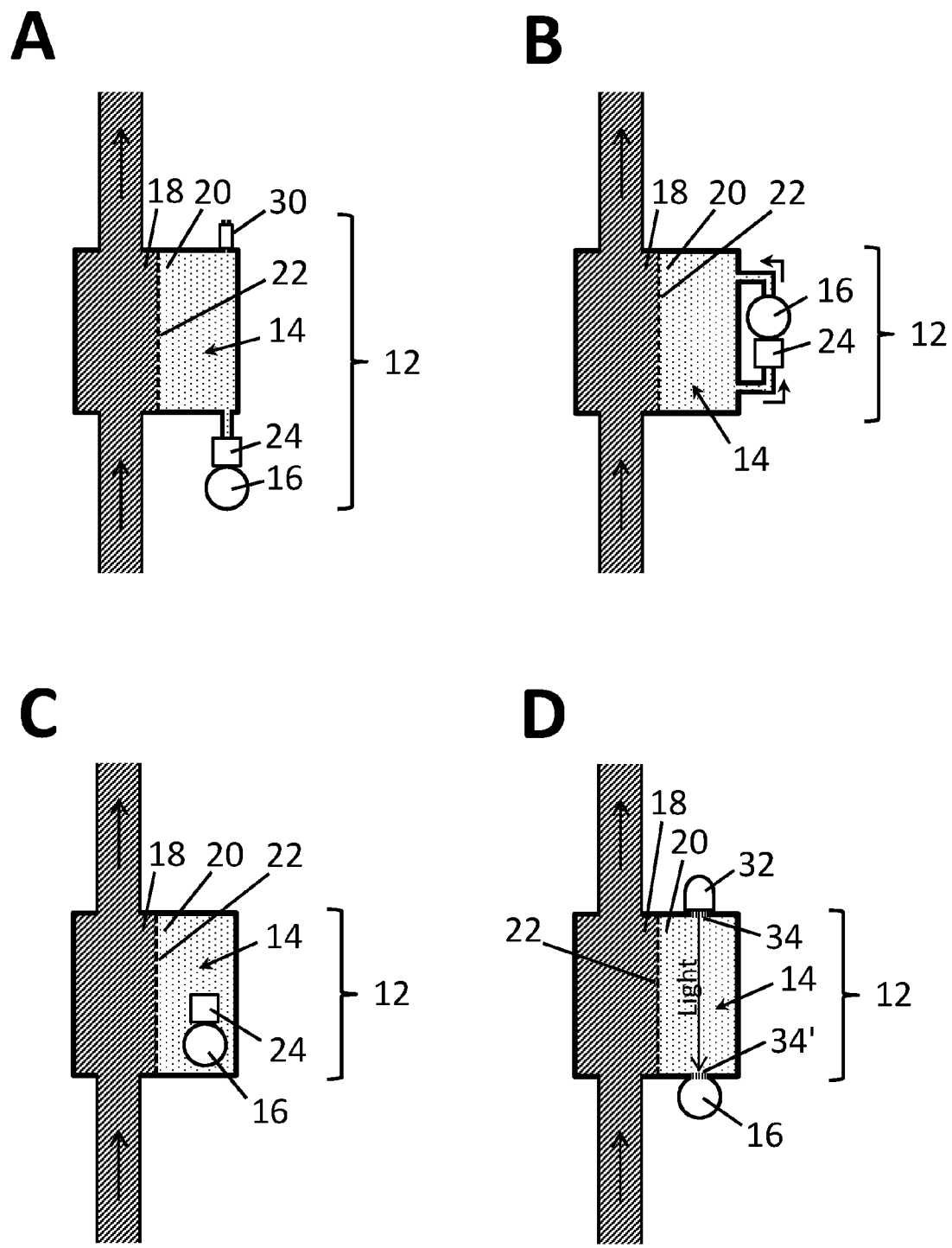
FIG. 2 shows equilibration-measurement units according to different embodiments of the invention. (A) Equilibration-measurement unit with an aspirator, an gas phase and an apparatus for pressure compensation located outside of the equilibration chamber which comprises the gas phase. (B) Equilibration-measurement unit in which the gas used for determining the concentration of the inhalational anesthetic in the gas phase is returned to the equilibration chamber after passing through an aspirator and apparatus for determining the concentration of the inhalational anesthetic in the gas phase located outside of the equilibration chamber which comprises the gas phase. (C) Equilibration-measurement unit in which the aspirator and the apparatus for determining the concentration of the inhalational anesthetic in the gas phase are fully integrated (i.e. located within) into the equilibration chamber which comprises the gas phase. (D) Equilibration-measurement unit designed for spectroscopic determination of the concentration of the inhalational anesthetic in the gas phase through windows in the equilibration chamber which comprises the gas phase.

FIG. 2 shows different embodiments of the equilibration-measurement unit 12 according to the present invention. Apart from the specific aspects pointed out below, construction and functioning of the equilibration-measurement units as depicted in FIG. 2A-C follows essentially the same principles as described above for the embodiment of FIG. 1.

In the embodiment depicted in FIG. 2A, the equilibration-measurement unit 12 comprises an aspirator 24, an apparatus for determining the concentration of the inhalational anesthetic in the gas phase 16 and an apparatus for pressure compensation 30. The apparatus for pressure compensation 30 is in this embodiment an opening that connects the gas phase 14 with the environmental air. Gas exchange through this opening is controlled by a pressure release valve (shown as a rectangle). The second compartment 20 is enclosed by gas-impermeable walls and the membrane 22, which define the equilibration chamber. According to the exemplary embodiment shown in FIG. 2A, the aspirator 24, the apparatus for determining the concentration of the inhalational anesthetic in the gas phase 16 and the apparatus for pressure compensation 30 are located outside of the equilibration chamber/second compartment 20. While in the embodiment of FIG. 2A the apparatus for pressure compensation 30 is directly attached to the wall of the equilibration chamber, the aspirator 24 and the apparatus for determining the concentration of the inhalational anesthetic in the gas phase 16 are connected to the equilibration chamber/second compartment 20 through a short connecting line through which the aspirator 24 can aspirate gas of the gas phase 14 to deliver it to the apparatus for determining the concentration of the inhalational anesthetic in the gas phase 16 (which in this embodiment is in direct contact with the aspirator 24 without any connecting lines between them) for analysis.

According to the embodiment shown in FIG. 2B, the equilibration-measurement unit 12 comprises an aspirator 24 and an apparatus for determining the concentration of the inhalational anesthetic in the gas phase 16, both of which are located outside of the equilibration chamber/second compartment 20. The aspirator 24 and an apparatus for determining the concentration of the inhalational anesthetic in the gas phase 16 are linked to the equilibration chamber/second compartment 20 by connecting lines that allow the aspirator to aspirate gas from the gas phase 14 in order to deliver it to the apparatus for determining the concentration of the inhalational anesthetic in the gas phase 16 for analysis, and return the gas used for analysis to the gas phase 14 after it has passed through the aspirator 24 and the apparatus for determining the concentration of the inhalational anesthetic in the gas phase 16.

FIG. 2C shows an embodiment in which the equilibration-measurement unit 12 comprises an aspirator 24 and an apparatus for determining the concentration of the inhalational anesthetic in the gas phase 16 both of which are fully integrated into the second compartment 20 comprising the gas phase 14 (i.e. both are located within the equilibration chamber).

Full integration of the aspirator 24 and the apparatus for determining the concentration of the inhalational anesthetic in the gas phase 16 is also shown in the exemplary embodiments depicted in FIGS. 1 and 3-6. However, it is of course equally possible and also contemplated by the present invention to combine the arrangement as shown in any of FIGS. 1 and 3-6 with a construction of the equilibration-measurement unit 12 according to any of FIG. 2A, 2B or 2D, or other constructions of the equilibration-measurement unit 12 according to the present invention.

In the exemplary embodiment shown in FIG. 2D, the equilibration-measurement unit 12 has light-permeable sections 34 and 34' within the walls defining the second compartment 20 (i.e. within the walls of the equilibration chamber). A light source 32 is located outside of the second compartment 20 such that it directs light (shown as an arrow) through the light-permeable section 34, the second compartment 20 and the light-permeable section 34' to the apparatus for determining the concentration of the inhalational anesthetic in the gas phase 16. Thus, the arrangement according to this embodiment allows to determine the concentration of the inhalational anesthetic in the gas phase 14 by IR-spectroscopy with a light source and a detector placed outside of the equilibration chamber.

Figure 3:
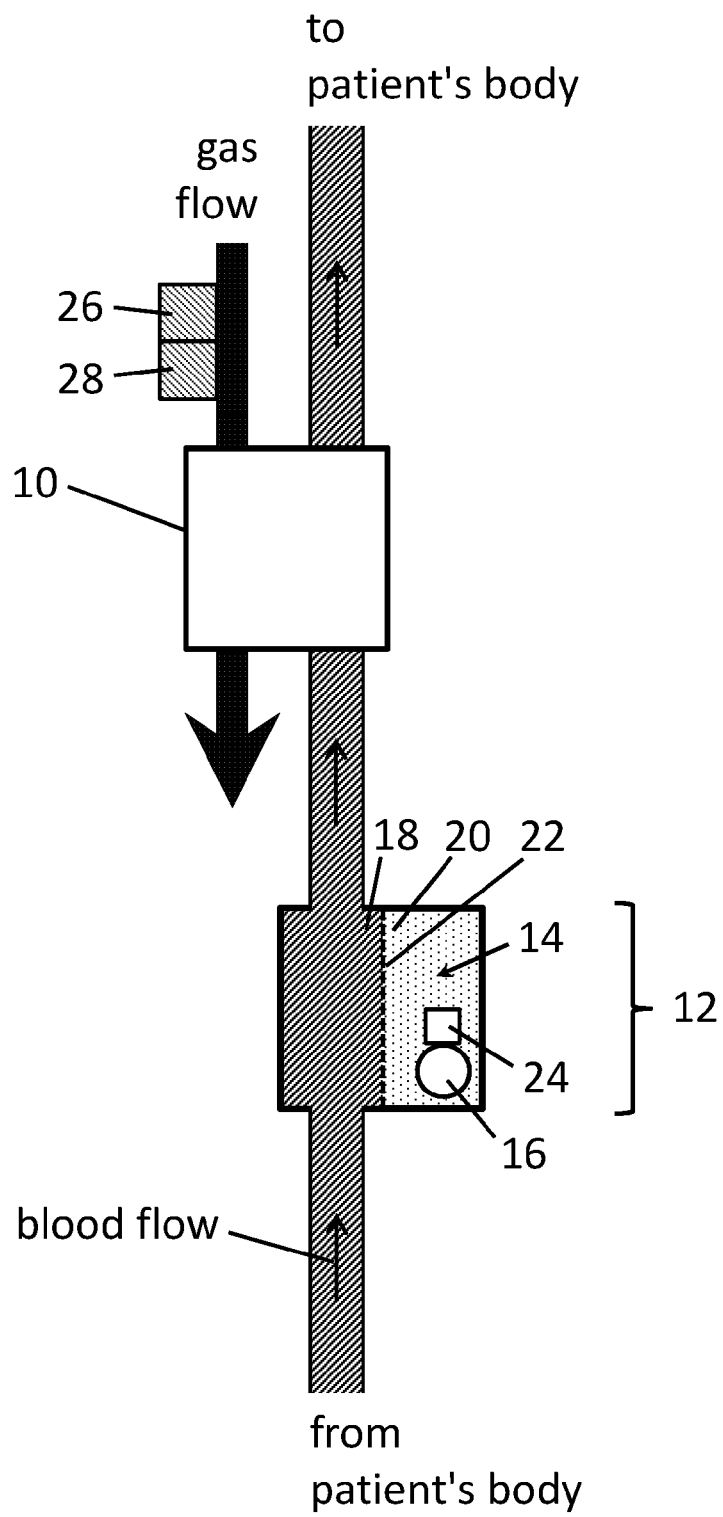
FIG. 3 shows an embodiment of the present invention in which the gas exchange chamber and the equilibration-measurement unit are arranged sequentially such that the blood flow first passes through the equilibration-measurement unit and subsequently passes through the gas exchange chamber.

FIG. 3 shows an alternative embodiment of the invention that differs from the embodiment of FIG. 1 by the arrangement of the gas exchange chamber 10 and the equilibration-measurement unit 12 with respect to the blood flow. While in the embodiment of FIG. 1 the gas exchange chamber 10 and the equilibration-measurement unit 12 are arranged such that the blood flow passes them in parallel, in the embodiment of FIG. 3 they are arranged serially, i.e. the blood oxygenator device is configured such that the blood flow through the blood oxygenator device first passes through the equilibration-measurement unit 12 and subsequently passes through the gas exchange chamber 10.

Figure 4:
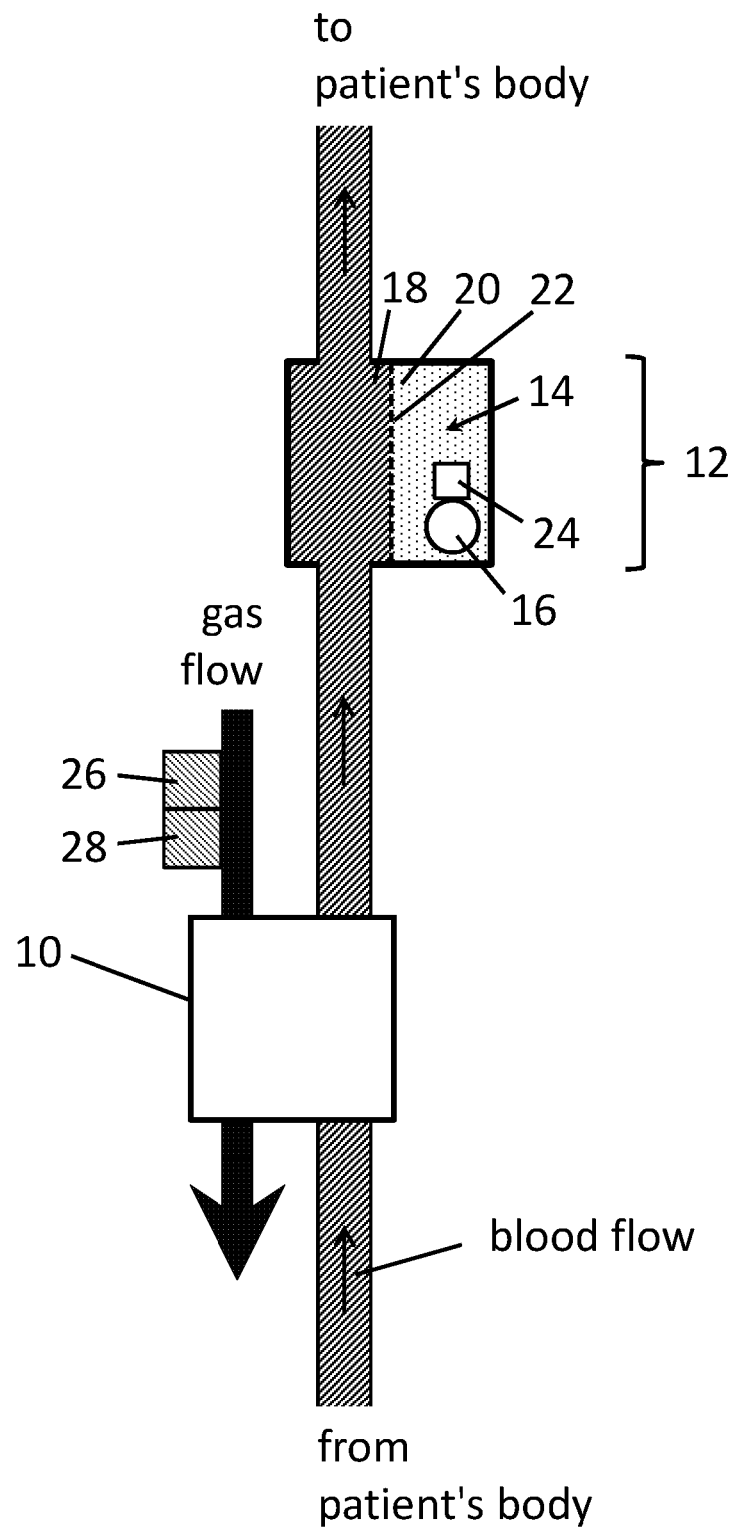
FIG. 4 shows an embodiment of the present invention in which the gas exchange chamber and the equilibration-measurement unit are arranged sequentially such that the blood flow first passes through the gas exchange chamber and subsequently passes through the equilibration-measurement unit.

The embodiment depicted in FIG. 4 differs from the embodiment shown in FIG. 3 by the order in which the blood flow passes through the gas exchange chamber 10 and the equilibration-measurement unit 12. Thus, the oxygenator device shown in FIG. 4 is configured such that the blood flow through the blood oxygenator device first passes through the gas exchange chamber 10 and subsequently passes through the equilibration-measurement unit 12.

Figure 5:
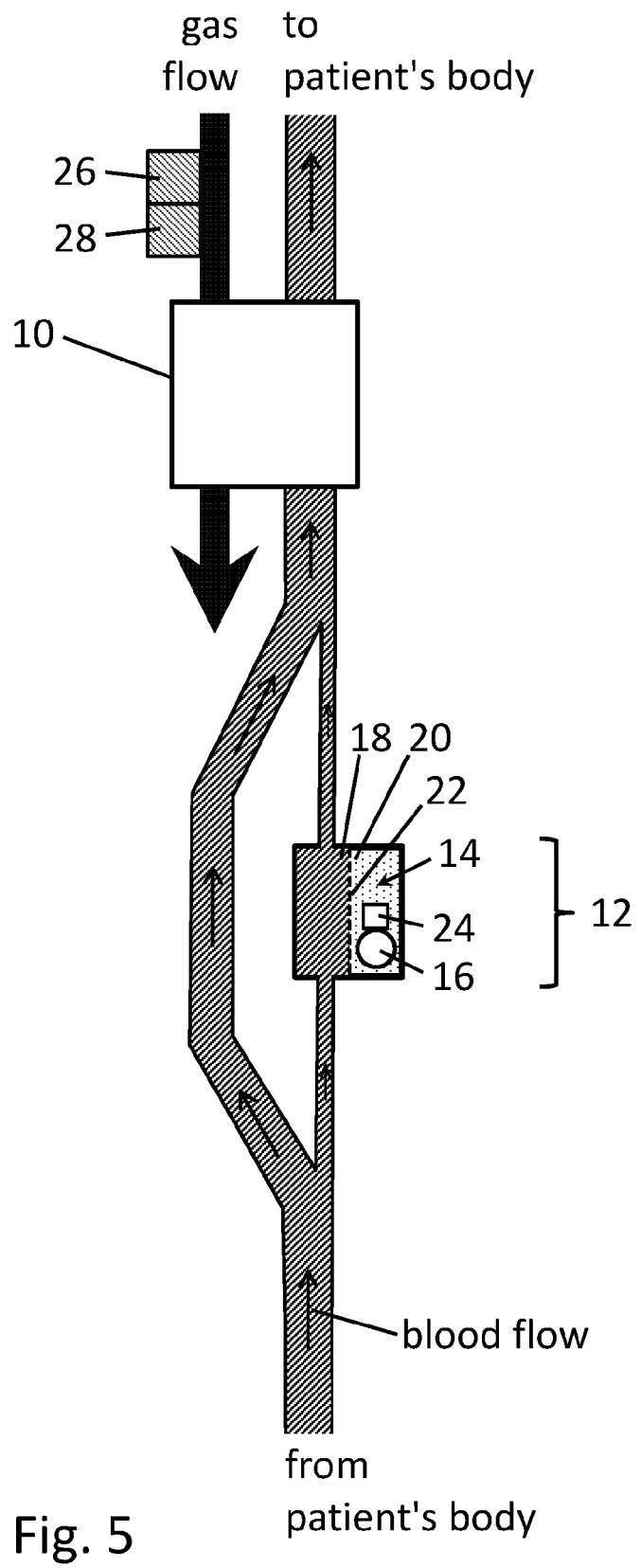
FIG. 5 shows an embodiment of the present invention in which the gas exchange chamber and the equilibration-measurement unit are arranged sequentially such that the blood flow first passes through/bypasses the equilibration-measurement unit and subsequently passes through the gas exchange chamber, wherein the blood flow is arranged such that a significant part of the blood flow bypasses the equilibration-measurement unit rather than flowing through it.

FIG. 5 shows an embodiment of the present invention in which the blood oxygenator device is constructed such that only a part of the blood flow through the oxygenator device passes through the equilibration-measurement unit 12, while another part of the blood flow through the oxygenator device bypasses the equilibration-measurement unit 12. Moreover, according to the embodiment shown in FIG. 5 the fluid lines of the branch bypassing the equilibration-measurement unit 12 have a larger diameter than the fluid lines of the branch passing through the equilibration-measurement unit 12. Therefore, the major part of the blood flow through the oxygenator device bypasses the equilibration-measurement unit 12, while only a minor fraction of the blood flow passes through the equilibration-measurement unit 12. The gas exchange chamber 10 and the equilibration-measurement unit 12 are arranged sequentially such that the blood flow first passes through/bypasses the equilibration-measurement unit 12 and subsequently passes through the gas exchange chamber 10.

Figure 6:
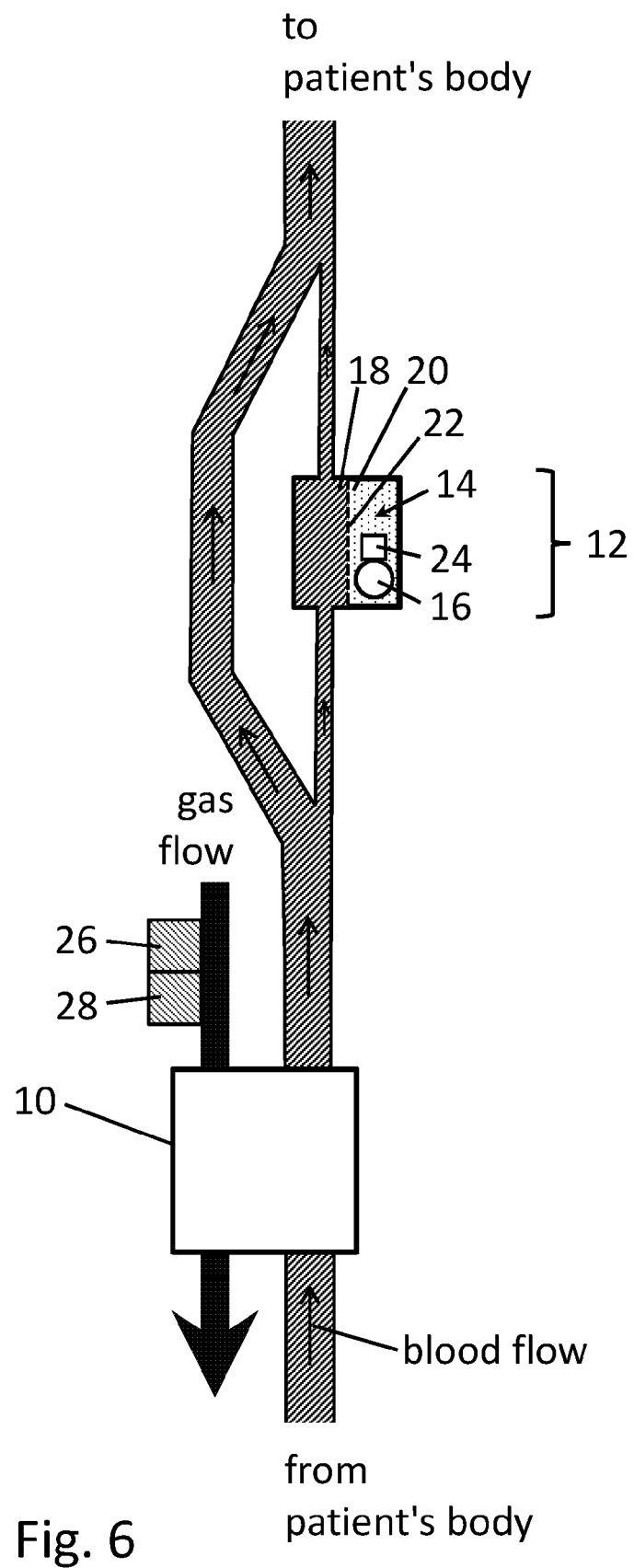
FIG. 6 shows an embodiment of the present invention in which the gas exchange chamber and the equilibration-measurement unit are arranged sequentially such that the blood flow first passes through the gas exchange chamber and subsequently passes through/bypasses the equilibration-measurement unit, wherein the blood flow is arranged such that a significant part of the blood flow bypasses the equilibration-measurement unit rather than flowing through it.

The embodiment shown in FIG. 6 differs from the embodiment shown in FIG. 5 by the order in which the blood passes through (or bypasses) the gas exchange chamber 10 and the equilibration-measurement unit 12. Thus, according to the embodiment depicted in FIG. 6, the gas exchange chamber 10 and the equilibration-measurement unit 12 are arranged such that the blood flow first passes through the gas exchange chamber 10 and subsequently passes through/bypasses the equilibration-measurement unit 12.

LIST OF REFERENCE SIGNS 10 gas exchange chamber
12 equilibration-measurement unit
14 gas phase
16 apparatus for determining the concentration of an inhalational anesthetic in the gas phase 14
18 first compartment
20 second compartment
22 membrane
24 aspirator
26 vaporizer
28 apparatus for admixing inhalational anesthetic/vaporized volatile anesthetic to the gas flow
30 apparatus for pressure compensation
32 light source
34 light-permeable section

The invention claimed is:
1. A blood oxygenator device comprising
a gas exchange chamber (10) in which gas exchange between a gas flow through said gas exchange chamber

(10) and blood of a patient passing through said gas exchange chamber (10) takes place; and an equilibration-measurement unit (12), wherein blood of the patient flows through the equilibration-measurement unit (12), wherein the equilibration-measurement unit (12) comprises a gas phase (14) which is in contact with the blood flowing through the equilibration-measurement unit (12) such that equilibration with respect to an inhalational anesthetic present in the blood occurs between the blood flowing through the equilibration-measurement unit (12) and the gas phase (14), and wherein said equilibration-measurement unit (12) comprises an apparatus (16) for determining the concentration of said inhalational anesthetic in the gas phase (14), wherein the blood oxygenator device is configured such that the blood flow through the blood oxygenator device is split up into two parts, wherein a first part of the blood flow passes through the gas exchange chamber (10) and a second part of the blood flow passes through the equilibration-measurement unit (12), and wherein, after the first part of the blood flow has passed through the gas exchange chamber (10) and the second part of the blood has passed through the equilibration-measurement unit (12), the first and the second part of the blood flow are merged again.

2. The blood oxygenator device according to claim 1, wherein the gas phase (14) does not undergo gas exchange with an environment except for gas exchange with the blood flowing through the equilibration-measurement unit (12).

3. The blood oxygenator device according to claim 1, wherein said equilibration-measurement unit (12) comprises a first compartment (18) through which the blood flowing through the equilibration-measurement unit (12) passes and a second compartment (20) in which the gas phase (14) is contained, wherein contact between the first compartment (18) and the second compartment (20) is provided by a membrane (22) which is impermeable to the blood, but permeable to the inhalational anesthetic.

4. The blood oxygenator device according to claim 1, wherein, the blood oxygenator device is configured such that the blood flow through the blood oxygenator device first passes through/bypasses the equilibration-measurement unit and subsequently passes through the gas exchange chamber or such that the blood flow through the blood oxygenator device first passes through the gas exchange chamber and subsequently passes through/bypasses the equilibration-measurement unit.

5. The blood oxygenator device according to claim 1, wherein said apparatus (16) for determining the concentration of the inhalational anesthetic in the gas phase (14) comprises or consists of a sensor, preferably the sensor for determining the concentration of the inhalational anesthetic in the gas phase (14) by an optical measurement, more preferably by IR-spectroscopy or Raman spectroscopy, or by acoustic measurements, more preferably by photoacoustic infrared spectroscopy, or by mass spectrometry or by measurements with a semiconductor gas sensor.

6. The blood oxygenator device according to claim 1, wherein said equilibration-measurement unit (12) comprises an aspirator (24) that delivers the gas phase (14) or a part of the gas phase (14) to the apparatus (16) for determining the concentration of the inhalational anesthetic in the gas phase (14).

7. The blood oxygenator device according to claim 1, wherein the blood oxygenator device comprises a first oxygenator and a second oxygenator, wherein said first oxygenator comprises an oxygenating chamber through which the gas flow passes, the oxygenating chamber of said first oxygenator serving as the gas exchange chamber (10) of the blood oxygenator device, while said second oxygenator comprises an oxygenating chamber through which no gas flow passes, the oxygenating chamber of said second oxygenator serving as equilibration-measurement unit (12) of the blood oxygenator device.

8. The blood oxygenator device according to claim 1, wherein the blood oxygenator device comprises a vaporizer (26) for vaporizing a volatile anesthetic, and an apparatus (28) for admixing a vaporized volatile anesthetic or inhalational anesthetic to the gas flow used for gas exchange in the gas exchange chamber (10).

9. The blood oxygenator device according to claim 1, wherein said inhalational anesthetic is an anesthetic gas, preferably xenon or nitrous oxide (laughing gas), or a volatile anesthetic, preferably a volatile anesthetic selected from the group consisting of sevoflurane, desflurane, isoflurane, enflurane and halothane.

10. The blood oxygenator device according to claim 1, wherein the gas exchange chamber (10) and the equilibration-measurement unit (12) are attached to the same base plate and/or enclosed in the same housing.

11. The blood oxygenator device according to claim 1, wherein said blood oxygenator device is for determining the concentration of the inhalational anesthetic in the blood of the patient, preferably the patient undergoing extracorporeal circulation, more preferably the patient undergoing extracorporeal circulation involving a cardiopulmonary bypass machine, the patient undergoing extracorporeal circulation in conjunction with extracorporeal membrane oxygenation (ECMO) or the patient undergoing extracorporeal circulation in conjunction with pumpless extracorporeal lung assist (PECLA).

12. Use of the blood oxygenator device as defined in claim 1 for determining the concentration of the inhalational anesthetic in the blood of the patient, wherein said use comprises the steps of a) passing the blood of said patient through the equilibration-measurement unit (12) of said blood oxygenator device;

b) determining the concentration of the inhalational anesthetic in the gas phase (14) comprised by said equilibration-measurement unit (12);

c) determining, based on the concentration of the inhalational anesthetic obtained in step b), the concentration of the inhalational anesthetic in the blood of the patient.

13. A method of manufacturing a blood oxygenator device having a gas exchange chamber (10) in which gas exchange between a gas flow through said gas exchange chamber (10) and blood of a patient passing through said gas exchange chamber (10) takes place; and an equilibration-measurement unit (12), wherein the blood of the patient flows through the equilibration-measurement unit (12), wherein the equilibration-measurement unit (12) comprises a gas phase (14) which is in contact with the blood flowing through the equilibration-measurement unit (12) such that equilibration with respect to an inhalational anesthetic present in the blood occurs between the blood flowing through the equilibration-measurement unit (12) and the gas phase (14), and wherein said equilibration-measurement unit (12) comprises an apparatus (16) for determining the concentration of said inhalational anesthetic in the gas phase (14), comprising the steps of
a) providing the gas exchange chamber (10) configured to allow for gas exchange between the gas flow through said gas exchange chamber (10) and the blood of the patient passing through said gas exchange chamber (10);
b) providing the equilibration-measurement unit (12) comprising
   a first compartment (18) configured to allow for the blood passing through it;
   a second compartment (20) in which the gas phase (14) is contained, wherein contact between the first compartment (18) and the second compartment (20) is provided by a membrane (22) which is impermeable to the blood, but permeable to the inhalational anesthetic, and wherein, preferably, said second compartment (20) is configured such that no gas exchange of the gas phase (14) with the environment occurs except for gas exchange through the membrane (22) with the blood passing through the first compartment (18); and
   the apparatus (16) for determining the concentration of the inhalational anesthetic in the gas phase (14);
c) providing fluid lines for transporting the blood flow; and
d) connecting the gas exchange chamber (10) and the equilibration-measurement unit (12) with said fluid lines such that the blood can be passed through the gas exchange chamber (10) and the equilibration-measurement unit (12).

14. A blood oxygenator device comprising
a gas exchange chamber (10) in which gas exchange between a gas flow through said gas exchange chamber (10) and blood of a patient passing through said gas exchange chamber (10) takes place; and
an equilibration-measurement unit (12), wherein the blood of the patient flows through the equilibration-measurement unit (12), wherein the equilibration-measurement unit (12) comprises a gas phase (14) which is in contact with the blood flowing through the equilibration-measurement unit (12) such that equilibration with respect to an inhalational anesthetic present in the blood occurs between the blood flowing through the equilibration-measurement unit (12) and the gas phase (14), and wherein said equilibration-measurement unit (12) comprises an apparatus (16) for determining the concentration of said inhalational anesthetic in the gas phase (14),
wherein the blood oxygenator device is configured such that the blood flow through the blood oxygenator device is split up into two parts, wherein a first part of the blood flow passes through the equilibration-measurement unit and a second part of the blood flow bypasses the equilibration-measurement unit, and wherein, after the first part of the blood flow has passed through the equilibration-measurement unit and the second part of the blood has bypassed the equilibration-measurement unit, the first and the second part of the blood flow are merged again.

15. The blood oxygenator device according to claim 14, wherein the gas phase (14) does not undergo gas exchange with the environment except for gas exchange with the blood flowing through equilibration-measurement unit (12).

16. The blood oxygenator device according to claim 14, wherein said equilibration-measurement unit (12) comprises a first compartment (18) through which the blood flowing through the equilibration-measurement unit (12) passes and a second compartment (20) in which the gas phase (14) is contained, wherein contact between the first compartment (18) and the second compartment (20) is provided by a membrane (22) which is impermeable to the blood, but permeable to the inhalational anesthetic.

17. The blood oxygenator device according to claim 14, wherein said apparatus (16) for determining the concentration of the inhalational anesthetic in the gas phase (14) comprises or consists of a sensor, preferably a sensor for determining the concentration of the inhalational anesthetic in the gas phase (14) by optical measurements, more preferably by IR-spectroscopy or Raman spectroscopy, or by acoustic measurements, more preferably by photoacoustic infrared spectroscopy, or by mass spectrometry or by measurements with a semiconductor gas sensor.

18. The blood oxygenator device according to claim 14, wherein said equilibration-measurement unit (12) comprises an aspirator (24) that delivers the gas phase (14) or a part of the gas phase (14) to the apparatus (16) for determining the concentration of the inhalational anesthetic in the gas phase (14).

19. The blood oxygenator device according to claim 14, wherein the blood oxygenator device comprises a first oxygenator and a second oxygenator, wherein said first oxygenator comprises an oxygenating chamber through which a gas flow passes, the oxygenating chamber of said first oxygenator serving as gas exchange chamber (10) of the blood oxygenator device, while said second oxygenator comprises an oxygenating chamber through which no gas flow passes, the oxygenating chamber of said second oxygenator serving as equilibration-measurement unit (12) of the blood oxygenator device.

20. The blood oxygenator device according to claim 14, wherein the blood oxygenator device comprises a vaporizer (26) for vaporizing a volatile anesthetic, and an apparatus (28) for admixing a vaporized volatile anesthetic or inhalational anesthetic to the gas flow used for gas exchange in the gas exchange chamber (10).

* * * * *